US006605092B2

(12) United States Patent
Grumberg et al.

(10) Patent No.: US 6,605,092 B2
(45) Date of Patent: Aug. 12, 2003

(54) GEOMETRICAL POSITIONING OF DRILLING IN MEDICAL APPLICATIONS

(76) Inventors: Manfred Grumberg, 64 Bania Street, Haifa, 34980 (IL); Zvi Laster, Mobile Post Office, Ponya Elite, Lower Galilee, 15208 (IL)

(*) Notice: Subject to any disclaimer, the term of this patent is extended or adjusted under 35 U.S.C. 154(b) by 110 days.

(21) Appl. No.: 09/992,019

(22) Filed: Nov. 26, 2001

(65) Prior Publication Data

US 2003/0100908 A1 May 29, 2003

(51) Int. Cl.$^7$ .................... A61B 17/56

(52) U.S. Cl. .................... 606/96; 433/76

(58) Field of Search .................... 606/80, 96, 97, 606/98; 408/16, 186, 241 G; 433/76

(56) References Cited

U.S. PATENT DOCUMENTS

| | | | | | |
|---|---|---|---|---|---|
| 3,906,640 | A | * | 9/1975 | Sosa | 33/263 |
| 4,779,319 | A | * | 10/1988 | Juengel | 29/57 |
| 4,803,976 | A | * | 2/1989 | Frigg et al. | 606/97 |
| 4,824,367 | A | * | 4/1989 | Rosenstiel et al. | 433/75 |
| 5,411,503 | A | * | 5/1995 | Hollstien et al. | 606/86 |
| 5,540,691 | A | * | 7/1996 | Elstrom et al. | 606/64 |
| 5,741,096 | A | * | 4/1998 | Olds | 408/1 R |
| 5,915,962 | A | | 6/1999 | Rosenlicht | |
| 5,954,769 | A | | 9/1999 | Rosenlicht | |
| 5,967,777 | A | | 10/1999 | Klein et al. | |
| 6,062,856 | A | | 5/2000 | Sussman | |
| 6,162,228 | A | * | 12/2000 | Durham | 606/96 |
| 6,413,022 | B1 | * | 7/2002 | Sarh | 408/76 |
| 6,536,100 | B2 | * | 3/2003 | Sarh et al. | 29/709 |
| 2002/0164217 | A1 | * | 11/2002 | Peterson | 408/1 R |

* cited by examiner

*Primary Examiner*—Eduardo C. Robert
(74) *Attorney, Agent, or Firm*—Mark M. Friedman

(57) ABSTRACT

A system and a method for positioning a drill, having a drill bit with a central axis, for drilling a subsequent hole in a bone at a predetermined distance from and in a predetermined orientation in respect to a reference hole, is disclosed. The system comprises a reference insert, configured to be inserted into the reference hole, and adapted to establish a reference guideline, the reference guideline being of the predetermined orientation; and, an alignment mechanism, configured to be attached to the drill, the alignment mechanism adapted to be fixed at the predetermined distance from and parallel to the central axis of the drill bit, the alignment mechanism including an optical device for colinearly aligning an alignment axis of the alignment mechanism with the reference guideline.

50 Claims, 8 Drawing Sheets

GEOMETRICAL POSITIONING OF DRILLING IN MEDICAL APPLICATIONS

FIELD AND BACKGROUND OF THE INVENTION

The present invention relates to the positioning and drilling of holes for the fixation of surgical implants and, more particularly, to an optical system and a method to assist a surgeon, and more particularly a dental implantologist or an orthopedic surgeon, in drilling at a predetermined location, distance and angulations relative to references.

A diverse variety of surgical and dental prostheses and appliances are affixed, permanently or temporarily, to the bone of a patient using bone screws, implants, nails, plates, pins or other fasteners. A major problem encountered by the surgeon is the drilling of holes for securing such appliances in the bone in the correct location, properly spaced from one another, and correctly oriented in space relative to one another.

Failure to place and align the holes properly can lead to many complications including improper fitting of the appliance, as well as damage to the bone and associated vascular and nervous tissues. When a load is placed on an appliance secured to holes that have been improperly placed and oriented, strains are placed on the bone that can damage the bone, lead to failure of the implant or secondary infection.

At the present time, in most cases such holes are typically drilled free-hand. In some cases the initial drilling of the holes is guided by template. In common orthopedic practice, when holes are drilled close to one another a mechanical guide may be used, but over long distances of bone (such as encountered in the limbs), placement of holes distant from one another is often guided by x-ray. This generally does not achieve precise localization and orientation, and especially angulation, and particularly not in three-dimensions since the x-ray provides only a two dimensional image. In addition, usage of x-rays involves the hazards of excessive and unnecessary radiation exposure to the patient as well as the surgeon and operating theater personnel.

Dental implants have become a standard dental procedure for the replacement of missing teeth. They do not use part of the original tooth as a foundation for the tooth replacement, but rather the drilling of holes directly into the jaw bone. In current practice, metal implants for artificial teeth are screwed into holes drilled into the human jaw. The artificial teeth have holes made in respect to the implanted screw heads. When mounted, the teeth are pushed over and screwed or cemented to posts that are screwed and fixed into the implants.

It is well understood, that for the teeth to slide properly into place, and for a snug fit with the implant posts, it is important to have parallel implants. This means that it is important to drill and enlarge the holes in the jaw parallel to one another, and located according to a predetermined plan. Today, the commonly used practice cannot assure the geometrical positioning of these holes when drilled and enlarged to the final size.

Attempts have been made to use devices to permit improved positioning of drilled holes for implants and other surgical appliances. U.S. Pat. No. 5,954,769 to Rosnlicht, U.S. Pat. No. 5,915,962 to Rosenlicht, U.S. Pat. No. 5,967,777 Klein, and U.S. Pat. No. 6,062,856 to Sussman disclose devices that are examples of attempted mechanical solutions to the difficulties encountered in placement and spacing of holes for implants. All of these, however, suffer from significant limitations. None of them achieves a sufficient and optimal degree of accuracy and precision of placement and orientation. The placement of orientation, spacing and angulation they allow is not precise in three dimensions. Because the devices rely on mechanical methodologies there is a limit to the distance over which they can be used and a limit to the distance over which they can be used with accuracy without increasing significantly the size of the guides. Accuracy is further diminished when these devices are used on curved or arching surfaces. Because they are mechanical devices they are bulky and inconvenient. Further, they are slow to use as they need to be screwed and fastened into place and then unscrewed. The mechanical guides and templates must be removed after partial drilling of the initial hole: they can only be maintained in place to allow drilling to the depth at which the drill head contacts the template and do not permit drilling to the full extent of the drill bit.

There is thus a widely recognized need for, and it would be highly advantageous to have, a system and a method to assist a surgeon, and more particularly a dental implantologist or an orthopedic surgeon, in drilling at a predetermined location, distance and angulations relative to references devoid of the above limitations.

SUMMARY OF THE INVENTION

According to the present invention there is provided a system and a method for the positioning and drilling of holes for the fixation of surgical implants and, more particularly, to an optical system and a method to assist a surgeon, and more particularly a dental implantologist or an orthopedic surgeon, in drilling at a predetermined location, distance and angulations relative to references.

According to one aspect of the present invention there is provided a system for positioning a drill for drilling a hole in a bone at a predetermined distance from, and in a predetermined orientation in respect to, a reference hole, the drill having a drill bit with a central axis, the system including: (a) a reference insert, configured to be inserted into the reference hole, and adapted to establish a reference guideline, the reference guideline being of the predetermined orientation; and, (b) an alignment mechanism, configured to be attached to the drill, the alignment mechanism adapted to be adjusted to the predetermined distance from and parallel to the central axis of the drill bit, the alignment mechanism including an optical device for colinearly aligning an alignment axis of the alignment mechanism with the reference guideline.

According to another aspect of the present invention there is provided a method for positioning a drill for drilling a subsequent hole in a bone at a predetermined distance from, and in a predetermined orientation in respect to, a reference hole, the drill having a drill bit with a central axis, the method comprising the steps of: (a) inserting a reference insert into the reference hole, the reference insert being adapted to establish a reference guideline, the reference guideline being of the predetermined orientation; (b) providing an alignment mechanism, attached to the drill, the alignment mechanism adapted to be fixed at the predetermined distance from and parallel to the central axis of the drill bit, the alignment mechanism including an optical device for colinearly aligning an alignment axis of the alignment mechanism with the reference guideline; (c) fixing the alignment mechanism at the predetermined distance; and, (d) aligning the alignment axis of the optical device of the alignment mechanism with the reference guideline, thereby positioning the drill at the predetermined distance from and in the predetermined orientation in respect to the reference hole.

According to further features in preferred embodiments of the invention described below, the reference insert has a central longitudinal axis and an upper surface, the upper surface being perpendicular to the central longitudinal axis, and the upper surface serving as a reference standard for the orientation of the hole in the bone.

According to still further features in the described preferred embodiments the reference insert has a central longitudinal axis and an upper surface, the upper surface being inclined at an obtuse angle relative to the central longitudinal axis, and the upper surface serving as a reference standard for the orientation of the hole in the bone.

According to still further features in the described preferred embodiments the reference insert is of a generally cylindrical shape.

According to still further features in the described preferred embodiments the reference insert has an upper surface, and the upper surface is lustrous.

According to still further features in the described preferred embodiments the reference insert is adapted for insertion into a previously drilled hole in bone.

According to still further features in the described preferred embodiments the reference insert is adapted for insertion into a prefabricated hole in a surgical fastener.

According to still further features in the described preferred embodiments the surgical fastener is a dental implant.

According to still further features in the described preferred embodiments the alignment mechanism is attached to the drill by an adjustable mechanism for adjusting the distance between the drill bit and the alignment mechanism.

According to still further features in the described preferred embodiments the alignment mechanism is attached to the drill by a slider for adjusting the distance between the drill bit and the alignment mechanism.

According to still further features in the described preferred embodiments the alignment mechanism is fixed at the predetermined distance from and parallel to the central axis of the drill bit by a tightening mechanism.

According to still further features in the described preferred embodiments a light source is connected to the reference insert, the light source producing a light beam for establishing the reference guideline.

According to still further features in the described preferred embodiments the light source is selected from the group consisting of a light emitting diode, a laser, and a fiber optic strand connected to a lamp.

According to still further features in the described preferred embodiments the light source includes a collimator for limiting a diameter and a dispersion angle of the light beam.

According to still further features in the described preferred embodiments the optical device includes at least two targets, the targets establishing the alignment axis of the alignment mechanism.

According to still further features in the described preferred embodiments the optical device includes a target support for maintaining in position the at least two targets.

According to still further features in the described preferred embodiments a first target of the at least two targets is an aperture on a first surface of the target support, the first surface being perpendicular to the alignment axis.

According to still further features in the described preferred embodiments a shape of the aperture is selected from the group consisting of a circle, a slit, and a cross.

According to still further features in the described preferred embodiments a shape of the aperture is filled with a filter, the filter having imprinted thereon an indicator marking.

According to still further features in the described preferred embodiments a second target of the at least two targets is placed on a second surface of the target support, the second surface being interior of the target support and parallel to and opposite to the first surface.

According to still further features in the described preferred embodiments the second target is an indicator marking.

According to still further features in the described preferred embodiments the target support is a cylindrical tube.

According to still further features in the described preferred embodiments the target support is a prism, the prism having at least three surfaces.

According to still further features in the described preferred embodiments, a first target of the at least two targets is placed on a first plane of the prism, the first plane being parallel to a first surface of the prism; a second target of the at least two targets is placed on a second plane of the prism, the second plane being parallel to a second surface of the prism; and, a third surface of the prism is a mirror.

According to still further features in the described preferred embodiments the reference guideline and the alignment axis are colinearly aligned by the light beam illuminating all of the at least two targets.

According to still further features in the described preferred embodiments the optical device includes a light source, the light source producing a light beam.

According to still further features in the described preferred embodiments the light source is selected from the group consisting of a light emitting diode, a laser, and a fiber optic strand connected to a lamp.

According to still further features in the described preferred embodiments the light source includes a collimator for limiting a diameter and a dispersion angle of the light beam.

According to still further features in the described preferred embodiments the optical device further includes a target, the target being fixed in position in the optical device and adapted to establish the alignment axis.

According to still further features in the described preferred embodiments the reference insert includes a mirror on the reference insert, the mirror being adapted to establish the reference guideline.

According to still further features in the described preferred embodiments the mirror is on an upper surface of the reference insert.

According to still further features in the described preferred embodiments the reference insert is hollow, forming a cavity, and the mirror is placed within the cavity.

According to still further features in the described preferred embodiments the light source and the target are fixed in position in the optical device such that the alignment axis is colinearly aligned with the reference guideline when the light beam incident on the mirror produces a reflected beam, and the reflected beam is colinear with the alignment axis of the target.

According to still further features in the described preferred embodiments the optical device includes a prism, wherethrough the light beam and the reflected beam pass, the prism having at least three faces.

According to still further features in the described preferred embodiments the faces are both reflective and transparent to light.

According to still further features in the described preferred embodiments the light beam first penetrates a first face of the at least three faces, such that the light beam is bent so as to pass through a second face of the at least three faces and the light beam produces a first image on a third face of the at least three faces; the second face is placeable opposite the reference insert, such that the beam is incident on the reference insert, and the reflected beam passes through the second face so as to be reflected by the first face to produce a second image on the third face; and, the first image and the second image are coincident such that only a single representation of the light beam is produced on a plane parallel to the third face when the alignment axis and the reference guideline are colinearly aligned.

According to still further features in the described preferred embodiments the prism has adjustable angles.

According to still further features in the described preferred embodiments the optical device includes a threaded fiber optic array with a plurality of fibers with two ends.

According to still further features in the described preferred embodiments the reference insert includes a mirror on an upper surface of the reference insert, the mirror being adapted to establish the reference guideline.

According to still further features in the described preferred embodiments the plurality of fibers includes at least one transmitting fiber, with a light source connected to a first end of the two ends, and at least one receiving fiber, with a light receptor at a first end of the two ends.

According to still further features in the described preferred embodiments the at least one transmitting fiber and the at least one receiving fiber are adapted to establish the alignment axis such that a light beam transmitted from a second end of the at least one transmitting fiber incident upon the mirror and reflected by the mirror is received by the first end of the at least one receiving fiber of the optical device only when the alignment axis and the reference guideline are colinearly aligned.

According to still further features in the described preferred embodiments a display element is connected to a second end of the at least one receiving fiber of the optical device.

According to still further features in the described preferred embodiments the display element is selected from the group consisting of a lens on the second end of the at least one receiving fiber, a miniature screen, an optical display, a photosensitive cell and a light detector.

According to still further features in the described preferred embodiments the light detector is connected to a signaling device.

According to still further features in the described preferred embodiments the signaling device produces an audible signal.

According to still further features in the described preferred embodiments the system is used for drilling the hole in bone for a dental implant.

According to still further features in the described preferred embodiments the system is used for drilling the hole in bone for an orthopedic fixation appliance.

According to still further features in the described preferred embodiments the method is used for drilling the hole in bone for a dental implant.

According to still further features in the described preferred embodiments the method is used for drilling the hole in bone for an orthopedic fixation appliance.

The present invention successfully addresses the shortcomings of the presently known configurations by providing a system and method for the positioning and drilling of holes for the fixation of surgical implants and, more particularly, to an optical system and a method to assist a surgeon, and more particularly a dental implantologist or an orthopedic surgeon, in drilling at a predetermined location, distance and angulations relative to references. It is an object of the present invention to provide means for drilling and enlarging consecutive holes, at a predetermined distance to optimize the orientation of holes so as to support the implants without affecting the strength of the bone.

Still another object of the present invention is to provide an optical arrangement that enables alignment of drilling at a predetermined angle to an existing hole at a predetermined distance, by means of auto-collimation or by means of target alignments. A particular case is the drilling and enlarging the holes for the implants with their central axes parallel to each other, to assure optimal loading and minimal stress on the implants.

Still another object of this invention is to provide guidance for drilling according to a predetermined drilling plan.

Still another object of the present invention is to provide the above-mentioned feature without altering the drilling tools, methods and procedures in use today.

Still a further object is to guide drilling up to the full depth of the holes, and allowing use of the full range of sizes of drill bit, up to the final diameter.

A further object is to provide a time saving method for guidance of drilling of medical holes which presents no hazard to the patient, including, for example, avoiding the hazard of radiation exposure which is inherent in the use of x-ray localization for guidance in drilling positioning.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
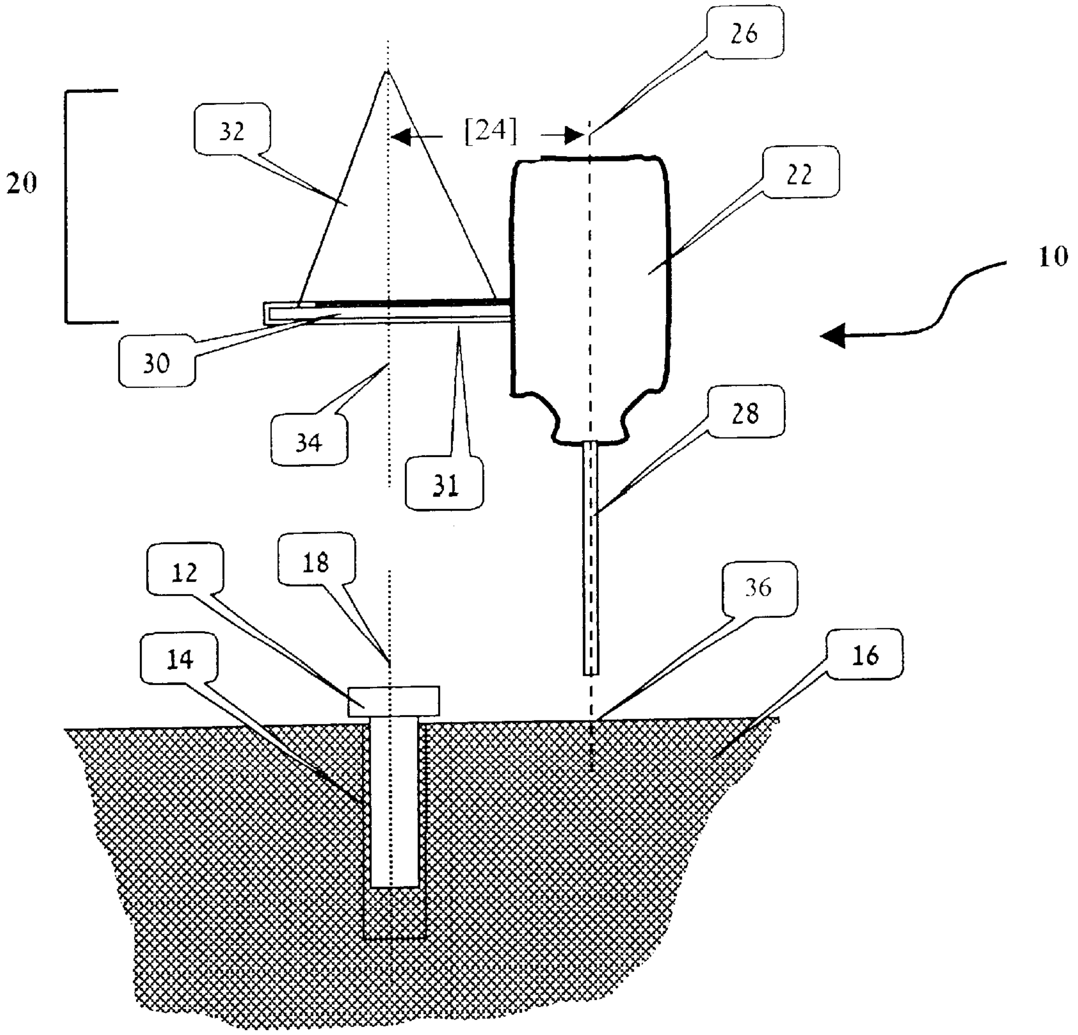
FIGS. 1*a* and *b* are schematic illustrations illustrating the principles of construction and operation of the system of the present invention.

The present invention is of a system and a method for the positioning and drilling of holes for the fixation of surgical implants which can be used to assist a surgeon, and more particularly a dental implantologist or an orthopedic surgeon, in drilling at a predetermined location, distance and angulations relative to references. Specifically, the present invention provides a system and a method that can be used for drilling a hole along a line that is at a predetermined geometrical position with respect to a reference, such as a previously drilled hole, by means of optical alignment. The previously drilled hole may be (a) a hole previously drilled in bone, or (b) it may be a hole (including a notch, indentation, cavity or other positioning means) previously drilled into a surgical fastener such as a screw, pin, nail, implant, or plate, for example; the fastener with the reference hole within having already been implanted into bone or some other tissue, or (c) it may be a hole within a template attached to the surgical fastener or to a drilled hole in bone. Specifically envisioned as being encompassed by the present invention is a previously drilled hole within a dental implant. Further, specifically envisioned as being encompassed by the present invention is use of the system and method for the positioning and drilling of holes for the fixation of surgical implants according to the present invention in humans as well as in other animal species.

The principles and operation of a system and a method for the positioning and drilling of holes for the fixation of surgical implants according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
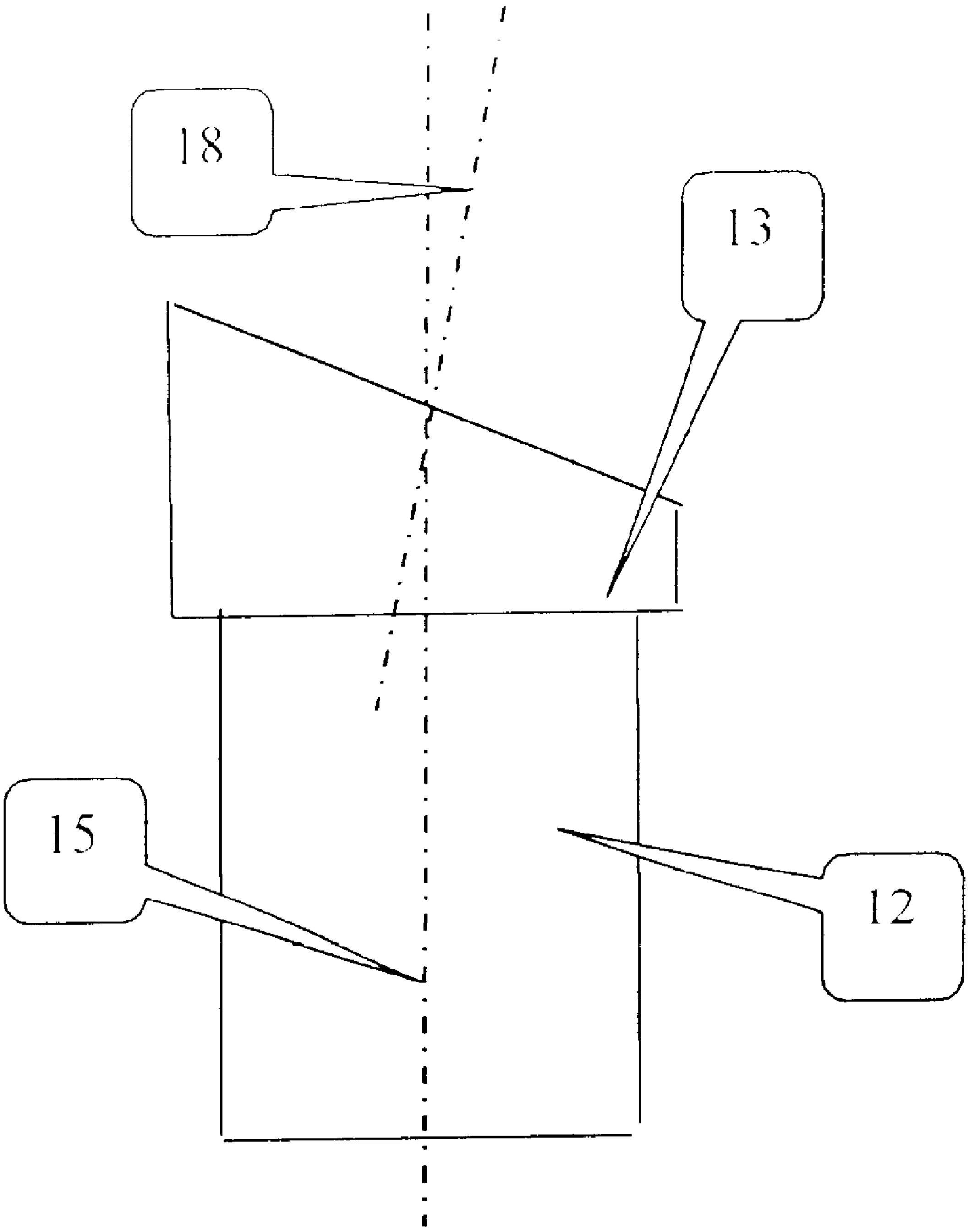

Referring now to the drawings, FIG. 1 illustrates the general principles of construction and operation of the system for positioning and drilling of holes for the fixation of surgical implants according to the present invention, which is referred to hereinunder as system 10. System 10 may be used for drilling holes for all types of surgical implants and appliances. In the following description, reference will be made to "implants" which may be cylindrical, screw-type, pin-type or any other type of implant or appliance as is known in the art. The descriptions hereinunder of dental and orthopedic applications are merely exemplary and should not be regarded as in anyway limiting as to the invention. A reference insert 12 is inserted into a previously drilled reference hole 14 in bone 16. Reference hole 14 is drilled by methods standard in the art. Alternatively, reference hole 14 is a predrilled hole or notch within a surgical fastener or template, the surgical fastener or template being in place already in the bone or other tissue of the patient. For the purposes of this specification and accompanying claims, the term "surgical fastener" is used to refer to such surgically applied elements for fixing surgical appliances in place, in bone or other tissues, including screws, pins, nails, implants, templates, wires, plates or other such fasteners. Reference insert 12 serves as a guide reference by creating an initial reference line 18. Reference line 18 is of a predetermined desired orientation, that is at a predetermined angle to reference hole 14. As illustrated in FIG. 1*b,* an upper surface 13 of reference insert 12 may be at any angle relative to the central axis 15 of the reference insert 12 (and therefore reference hole 14) so as to guide the drilling of a hole at the same angle (orientation) relative to the initial hole. In FIG. 1*a* upper surface 13 is at a 90 degree angle to central axis 15 of insert 12, while in FIG. 1*b,* upper surface 13 is inclined at an obtuse angle (greater than 90 degrees, but less than 180 degrees) relative to central axis 15 of insert 12. By rotating insert 12 around central axis 15 an angle of orientation of upper surface 13 complementary to the obtuse angle, that is inclined in the opposite direction, is achieved. For the purposes of this specification and the accompanying claims, an incline of upper surface 13 termed "obtuse" is used to refer to any angle other than 90 degrees.

Where reference hole 14 is a predrilled hole in a surgical fastener, it is important to note that reference hole 14, and therefore reference line 18, may have an angle of orientation different from the angle of orientation of the hole into which the surgical fastener has been placed.

Reference insert 12 is of a shape suitable for insertion into reference hole 14 and is of such size as to fit firmly so as to maintain position and orientation but so as to be removable. Reference insert is preferably of an elongate, generally cylindrical shape. For dental purposes such a reference insert 12 ranges in size from 1 to 10 mm, preferably from 2 to 10 mm and most preferably from 2 to 4.5 mm. Reference insert 12 may be made of any biocompatible insert but preferably surface 13 is lustrous, that is, it is made of, or is covered with, a shiny, reflective material, that is, a material with a high gloss or shine that is highly reflective of light.

An alignment mechanism 20, is attached to a drill 22 using a slider, extendable joint, expandable mechanism, adjustable scissors- or caliper-type mechanism or other such connection that is capable of being adjusted by the surgeon to maintain a connection of a desired, variable distance from drill 22. Alignment mechanism 20 is set to maintain a predetermined desired distance (24) between the central alignment axis 34 of alignment mechanism 20 and central axis line 26 of drill 22 and drill bit 28. Distance 24 ranges from 2 through 500 mm, preferably from 7 to 30 mm for dental purposes and from 20 to 350 mm for orthopedic uses, as non-limiting examples. Alignment mechanism 20 is attached to drill 22 in such a manner so as to maintain alignment mechanism 20 parallel to central axis 26. Alignment mechanism 20 is aligned with reference line 18, as determined by reference insert 12 in reference hole 14, by aligning alignment axis 34 with reference line 18, maintaining axis 34 parallel to reference line 18 at the desired distance 24, permitting drilling by a drill bit 28 at the predetermined distance (24) and at an angle determined by reference line 18 in relation to axis 15 of reference hole 14. Full geometric positioning and orientation in three dimensions is achieved when reference and alignment is made to more than one reference line.

In a preferred embodiment of the present invention, alignment mechanism 20 is preferably attached to drill 22 by a slider 30, and drill 22 is preferably the drilling head of a surgical drilling handpiece. In a preferred embodiment of the present invention, the position of slider 30 in relation to drill 22 is adjustable by being movable and can be maintained in place in its set position, simply by friction or by use of tightening mechanism such as a screw, clamp or band as non-limiting examples. Alignment mechanism 20 preferably includes a distance indicator 31 such as distance markings marked by lines, grooves, notches, or other such markings in units such as millimeters or fractions thereof along alignment mechanism 20, a ruler, or other such measurement indicator that can be used in setting alignment mechanism 20 to the proper distance. One ordinarily skilled in the art will be capable of assembling such a configuration from commercially available components.

Another component of alignment mechanism 20, connected to slider 30, and moved by slider 30, is preferably an optical device 32 for alignment of alignment axis 34 (parallel to drill 22) with reference line 18. Optical device 32 has as alignment axis 34 an optical alignment axis that is maintained constantly parallel to central axis line 26 of drill 22 and drill bit 28. Optical device 32 and thus optical alignment line 34 can be adjusted by sliding slider 30 so as to be at the desired predetermined distance 24 from central axis line 26 of drill 22 and drill bit 28. This determines the distance between a new hole 36 to be drilled from the reference hole 14. When optical alignment line 34 is aligned with reference line 18 this permits new hole 36 to be drilled at the correct geometric position (orientation), parallel to reference line 18 at predetermined distance 24.

FIG. 2 illustrates a preferred embodiment of system 10. A light source 38 is attached to reference insert 12. In different configurations, light source 38 is attached to upper surface 13 of reference insert 12 or is embedded within reference insert 12 with an aperture on surface 13, as non-limiting examples. Light source 38 is, in various configurations, a light emitting diode (LED), a laser source, or the tip of a fiber optic strand whose other end is attached to a lamp (that is, a regular light source). Light source 38 has a narrow light beam 40. Preferably beam 40 has a dispersion angle of less than 10 degrees. In certain configurations, light source 38 includes a collimator that limits the diameter and the dispersion angle of beam 40. Preferably beam 40 has a diameter less than 2.5 mm. Light beam 40 defines reference line 18.

In a preferred embodiment, illustrated in FIGS. 2 *a–c,* optical device 32 includes a target support 42, with a narrow aperture 46 on a surface 44 of target support 42 that faces insert 12. Aperture 46 may be of any shape including a circle, a slit, or a cross-hair shape, as non-limiting examples, and may be left as an opening or may be filled with a transparent filter or lens, which may have imprinted thereon an indicator marking of a pattern such as a "bulls eye," "X" or cross hairs. At least two targets, (two are shown in FIG. 2, and are designated as 48 and 50), each at a different location on or along and within target support 42, define the optical axis or optical alignment line 34 of target support 42 and thus device 32. For example, in the embodiment illustrated in FIG. 2*b,* first target 48 is the circular opening formed by aperture 46. In the preferred embodiment illustrated in FIGS. 2 *a–c,* the surface on the interior of target support 42 parallel to and opposite surface 44 is a target surface (52). Surfaces 44 and 52 are perpendicular to optical alignment line 34 in the embodiment illustrated in FIG. 2*a,* (however, optical alignment line 34 may be bent as illustrated in FIG. 2*d* and described hereinunder.) Second target 50 in the preferred embodiment illustrated in FIG. 2*b* is a cross-shaped indicator marking on surface 52. The central point of intersection of targets 48 and 50, that is of optical line 34, on target surface 52 is designated target point 54. When light beam 40 illuminates target support 42 through aperture 46 (which is acting as the first target 48) on surface 44 of target support 42, and is centered on target point 54, the target support 42 and light beam 40 are coaxial. When light beam 40 strikes target point 54, surface 44 is being maintained perpendicular to beam 40. As target point 54 is maintained at predefined distance 24 from central axis line 26 of drill 22 and drill bit 28, drilling of new hole 36 will be at the correct geometric position.

Target support 42 is, in the preferred embodiment illustrated in FIGS. 2 *a–c,* a cylindrical tube, but may be a structure of any shape that supports and aligns at least two targets. In various preferred embodiments, the two targets may take various forms, being some combination of apertures and indicating markers, for example. Indicator markings, may be circles, lines, cross hairs or other such markings.

Figure 2A:
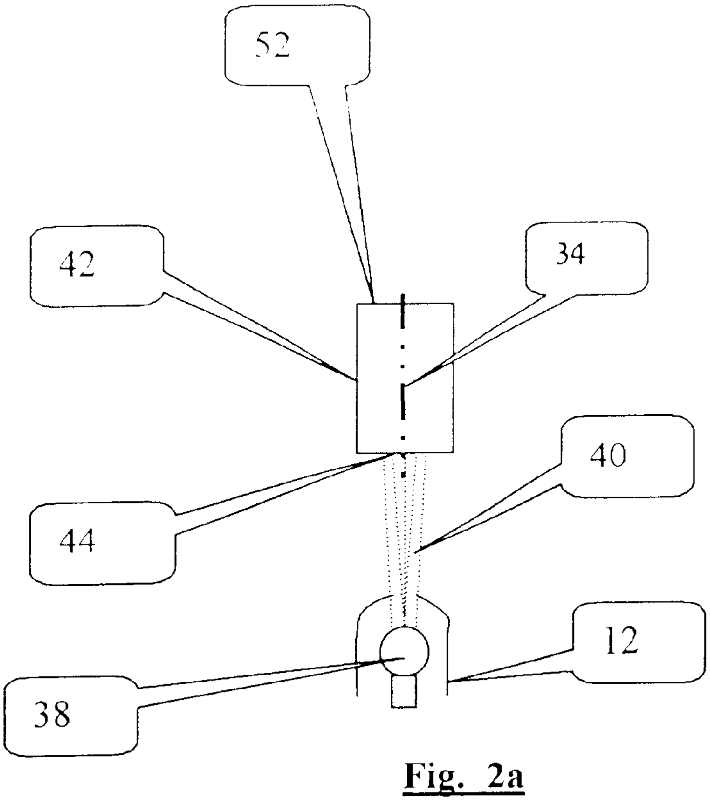
FIGS. 2*a–c* are schematic illustrations of a preferred embodiment of a system according to the present invention.
Figure 2B:
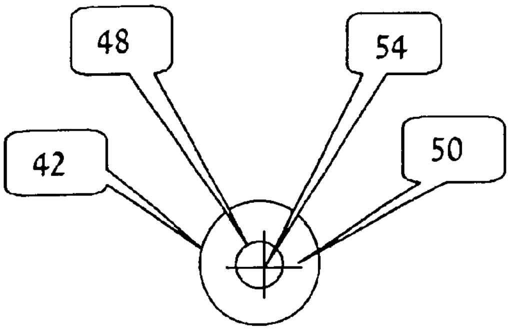
Figure 2C:
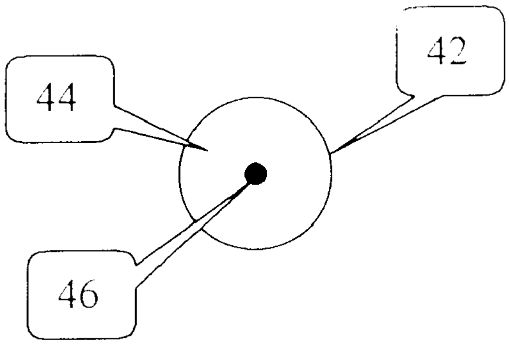
Figure 2D:
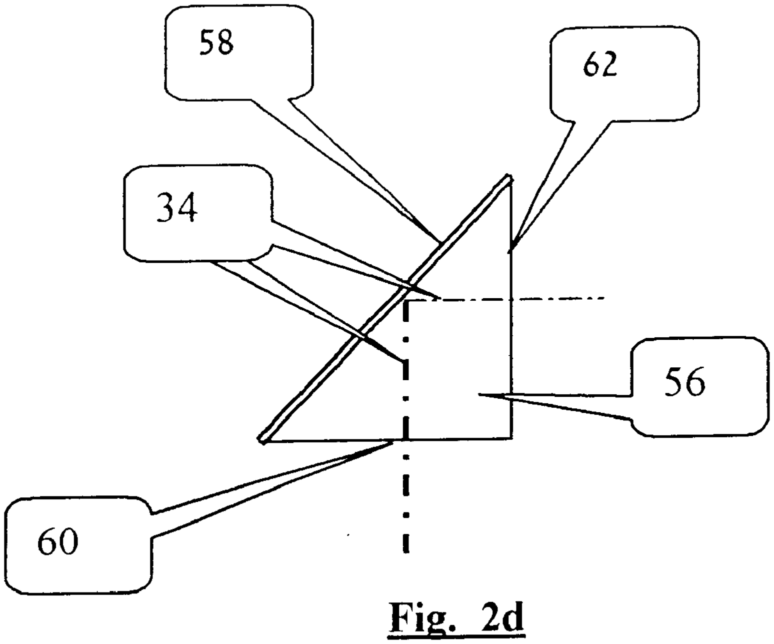
FIG. 2*d* is a schematic illustration of another preferred embodiment of a system according to the present invention.

Specifically envisioned as an alternate preferred embodiment of the present invention, is that as illustrated in FIG. 2*d,* in which an optical prism 56 is used in the place of a tube (as in FIG. 2*a*) as target support 42. On prism 56, face 58 is a mirror, while face 60 replaces surface 44 and target face 62 replaces target surface 52. At least two targets, preferably markings on faces 60 and 62, define optical alignment line 34. Prism 56 may be of any angle, equal to, or different from 90 degrees. A prism shaped embodiment of target structure 42 has several advantages. Because optical alignment line 34 is bent and folded, target structure 42 can be of a shorter length allowing it to fit better in the small space for example of the oral cavity. The prism shape also allows surface 62 to be directed more easily toward the surgeon operating system 10.

Figure 3:
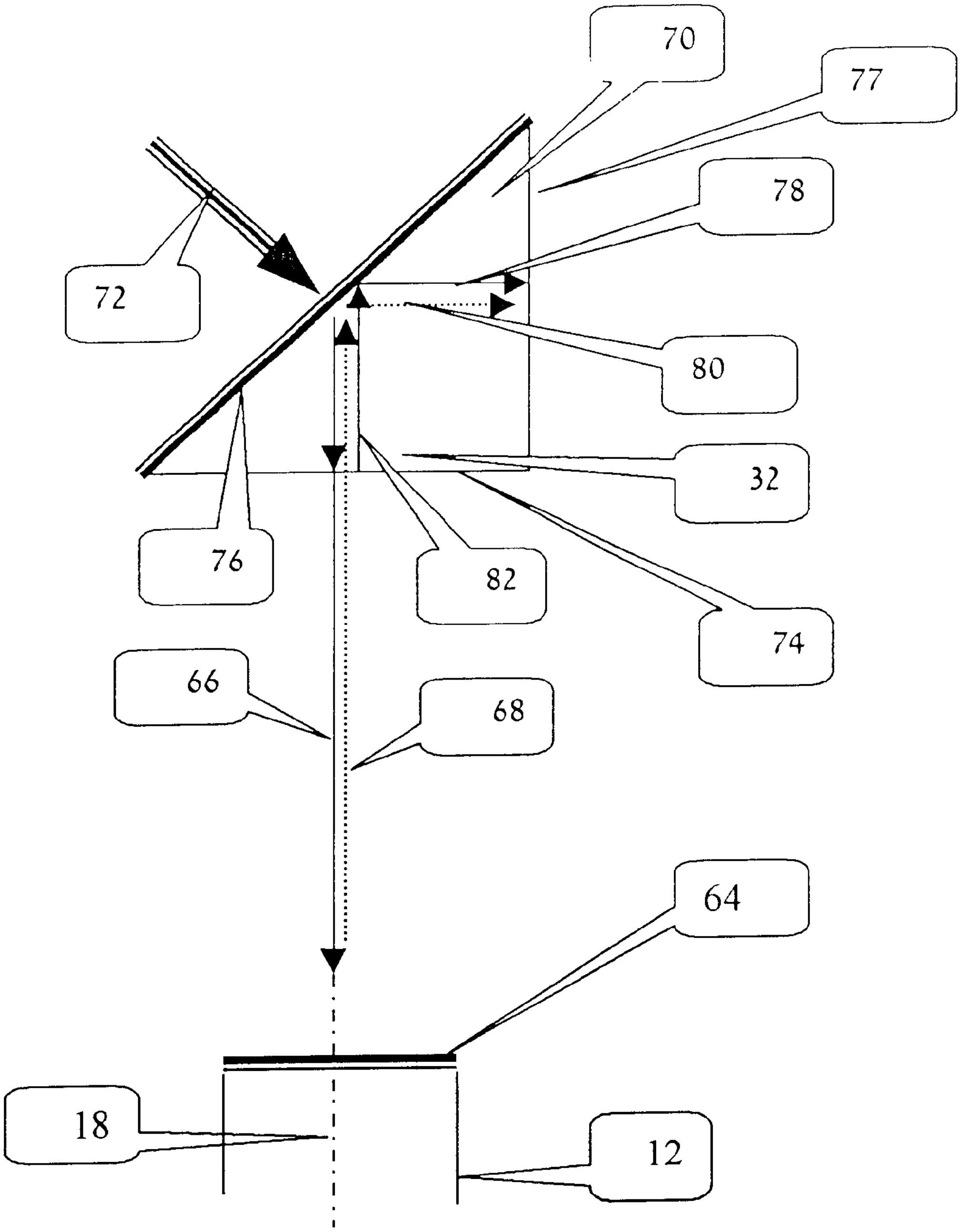
FIG. 3*a* is a schematic illustration of a further preferred embodiment of a system according to the present invention.
FIGS. 3*b–c* are schematic illustrations of a still further preferred embodiment of a system according to the present invention; and, FIGS. 3*d–e* schematically illustrate the use of a preferred embodiment of a system according to the present invention.
Figure 3:
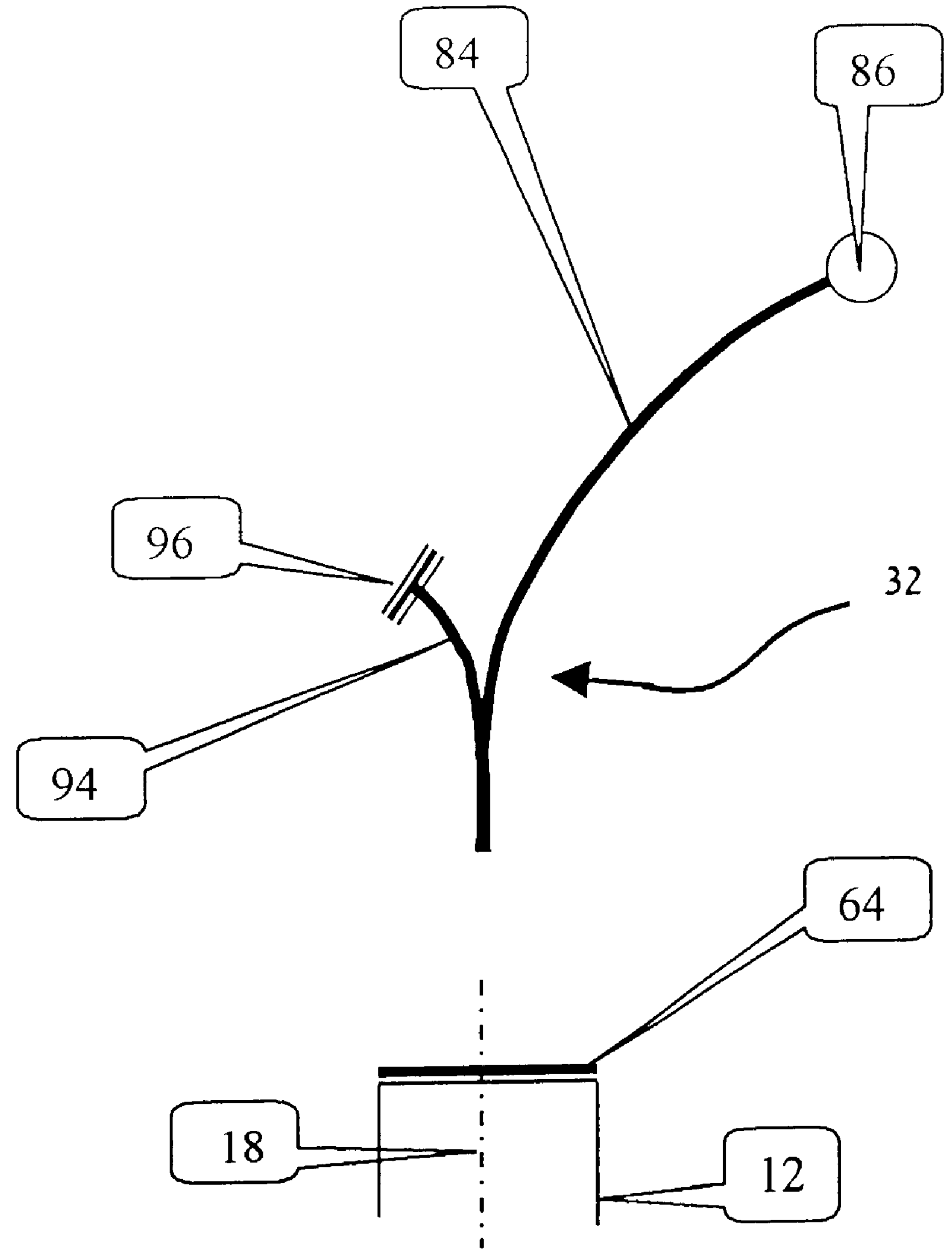
Figure 3:
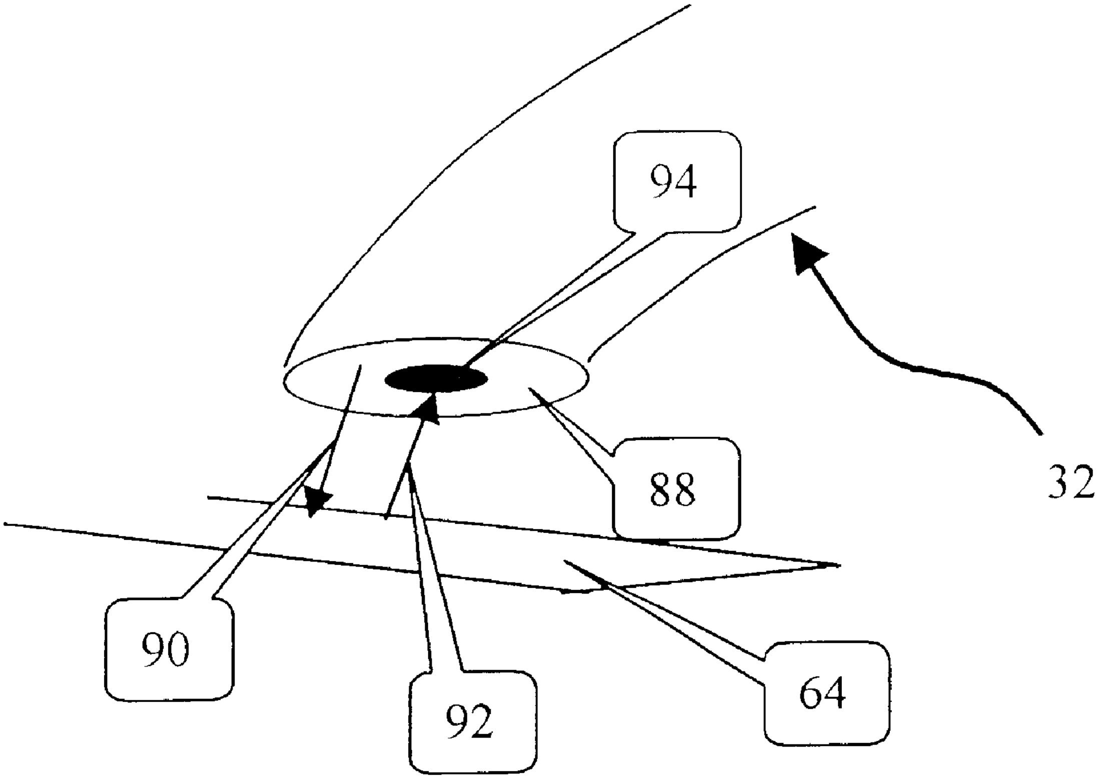
Figure 3:
Figure 3:
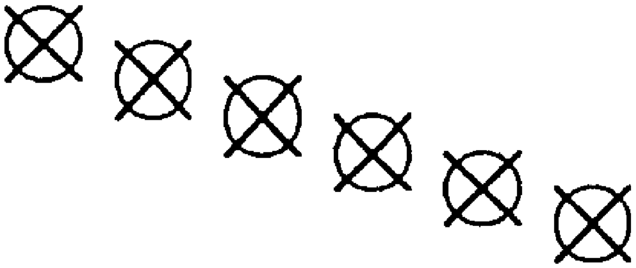

FIG. 3 illustrates yet another preferred embodiment of the system of the present invention. In this embodiment, on the upper surface (13 in FIG. 1) of insert 12 is a mirror 64. [In an alternative embodiment, insert 12 is a hollow cylinder and mirror 64 is placed inside the cylinder at the bottom of the cylinder.] Preferably mirror 64 has a small surface area and the center of mirror 64 is over reference line 18. A light beam 66 originates from optical device 32. The characteristics of the light beam 66 and the light source producing beam 66 are similar to those for the preferred embodiment described hereinabove and illustrated in FIG. 2, for example, beam 66 has a narrow diameter and angle of dispersion. Beam 66 impacts on mirror 64 and is reflected back to device 32 as a reflected beam 68. Only when optical device 32 is directly above mirror 64 and centered over the point which would correspond to reference line 18 in FIG. 1 and the line of sight (corresponding to optical alignment line 34 of FIG. 1) of optical device 32 is aligned precisely perpendicular to the surface of mirror 64 and thus of insert 12, will beam 66 and the reflected light 68 coincide.

As illustrated in FIG. 3*a,* in a preferred embodiment of the system of the present invention, optical device 32 can be configured as a prism 70. Prism 70 is such that each surface is partially reflective and partially transparent to light. Light originates from a light source through device 32 as a source beam 72. Beam 72 reflects from the lower surface 74 of prism 70 as beam 82 (which is then reflected from prism mirror face 76 as beam 78) and from the surface of mirror 64 as beam 68 which is then reflected from prism mirror face 76 as beam 80. When the two reflected beams 78 and 80 coincide, prism 70 (and thus optical device 32, as well as alignment mechanism 20) is in the correct aligned position. When optical device 32 and thus alignment mechanism 20 are not aligned, there will be multiple reflections of beam 72 off mirror 64 that are seen at surface 77, which would appear as seen in FIG. 3*d.* What is seen is multiple reflections, much as one sees when looking, from off center, into one of two parallel mirrors. When optical device 32 and thus alignment mechanism 20 are properly and precisely aligned, there will be only a single reflection of beam 72 off mirror 64 seen at surface 77, which would appear as seen in FIG. 3*e*.

In an alternate configuration prism 70 is of an adjustable angle, such that surfaces 74 and 77 can rotate in a synchronized fashion relative to mirror face 76, in the manner employed in a conventional overhead projector.

FIGS. 3*b* and 3*c* illustrates a further preferred embodiment in which optical device 32 is a threaded fiber optic array. Part of the fibers serves as a light conduit 84 from a light source 86. When the optical line (equivalent to 34 in FIG. 1) of a projected light beam 90 exiting from the ends (indicated by 88) of the transmitting fibers of light conduit 84 is centered on mirror 64 on insert 12 and is perpendicular to the surface of mirror 64, receiving fibers 94 will detect a reflected beam 92. Receiving fibers 94 will illuminate the reflected light 92 onto a light display 96. Light display 96 may be a lens on the fiber end, a miniature screen or other optical display or a photosensitive cell or other light detector, which can be connected, for example, to a signaling device which gives off an audible tone such as a buzz, when illuminated. In certain of those embodiments which feature a light detector, the light beam 72 used is of polarized light. The signal produced from the light detector reaches maximal intensity when the reflected light is maximally received. An audible signal allows the surgeon to make the alignment without have to visually align the axes, freeing the surgeon to be able to visually focus elsewhere, for example, at the drilling site.

The above described system for positioning and drilling of holes for the fixation of surgical implants will find use primarily in conjugation with a method for positioning and drilling of holes for the fixation of surgical implants. This method begins after, for example, the drilling of a reference hole 14 in bone using such methods as are standard in the surgical art; or the placement of a surgical fastener, containing a pre-fashioned hole therein which serves as reference hole 14. This method includes the steps of, for example, (a) inserting a reference insert 12 into reference hole 14 as described hereinabove so as to establish a reference line (18) of a predetermined orientation; (b) providing an alignment mechanism (20) connected to a drill 22, the alignment mechanism including an optical device (32) which is adapted and configured so as to establish an optical alignment axis (34), as described in the preferred embodiments, hereinabove; (c) fixing alignment mechanism 20 at a distance equal to predetermined requested distance 24 (preferably using slider 30) as described hereinabove; (d) aligning alignment mechanism 20 (including optical device 32) attached to drill 22 with the reference line of insert 12 as described hereinabove; and (e) drilling a new hole 36 at the predetermined distance 24 and parallel to the initial reference hole; and (f) as desired for additional hole placement and drilling, inserting insert 12 into new hole 36 and repeating steps c–f to drill further holes, or keeping insert 12 in reference hole 14, setting a new distance as in step (c) above and repeating steps d–f, as desired. Full geometric positioning and orientation in three dimensions is achieved when reference and alignment is made to more than one reference line.

Thus, the system and a method for the positioning and drilling of holes for the fixation of surgical implants at a predetermined location, distance and orientation relative to references of the present invention provides guidance for drilling according to a predetermined drilling plan without altering the drilling tools, methods and procedures in use today. The present invention provides the means for drilling and enlarging consecutive holes, at a predetermined distance to optimize the number of holes as to support the implants without affecting the strength of the bone and specifically provides an optical arrangement that enables alignment of drilling at a predetermined angle to an existing hole at a predetermined distance using target alignment. This is particularly useful for drilling and enlarging the holes for the implants with their central axes parallel to each other, to assure optimal loading and minimal stress on the implants. The system and method of the present invention permits drilling up to the full depth of the holes, and allows the use of the full range of sizes of drill bit, up to the final diameter. Finally the present invention provides a time saving method for guidance of drilling of medical holes, which presents no hazard to the patient.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for positioning a drill for drilling a hole in a bone at a predetermined distance from, and in a predetermined orientation in respect to, a reference hole, the drill having a drill bit with a central axis, the system comprising:

(a) a reference insert, configured to be inserted into the reference hole, and adapted to establish a reference guideline, said reference guideline being of the predetermined orientation; and, (b) an alignment mechanism, configured to be attached to the drill, said alignment mechanism adapted to be adjusted to the predetermined distance from and parallel to the central axis of the drill bit, said alignment mechanism including an optical device for colinearly aligning an alignment axis of said alignment mechanism with said reference guideline.

2. The system of claim 1, wherein said reference insert has a central longitudinal axis and an upper surface, said upper surface being perpendicular to said central longitudinal axis, and said upper surface serving as a reference standard for the orientation of the hole in the bone.

3. The system of claim 1, wherein said reference insert has a central longitudinal axis and an upper surface, said upper surface being inclined at an obtuse angle relative to said central longitudinal axis, and said upper surface serving as a reference standard for the orientation of the hole in the bone.

4. The system of claim 1, wherein said reference insert is of a generally cylindrical shape.

5. The system of claim 1, wherein said reference insert has an upper surface, and said upper surface is lustrous.

6. The system of claim 1, wherein said reference insert is adapted for insertion into a previously drilled hole in bone.

7. The system of claim 1, wherein said reference insert is adapted for insertion into a prefabricated hole in a surgical fastener.

8. The system of claim 7, wherein said surgical fastener is a dental implant.

9. The system of claim 1, wherein said alignment mechanism is attached to the drill by an adjustable mechanism for adjusting the distance between the drill bit and said alignment mechanism.

10. The system of claim 1, wherein said alignment mechanism is attached to the drill by a slider for adjusting the distance between the drill bit and said alignment mechanism.

11. The system of claim 1, wherein said alignment mechanism is fixed at the predetermined distance from and parallel to the central axis of the drill bit by a tightening mechanism.

12. The system of claim 1, wherein a light source is connected to said reference insert, said light source producing a light beam for establishing said reference guideline.

13. The system of claim 12, wherein said light source is selected from the group consisting of a light emitting diode, a laser, and a fiber optic strand connected to a lamp.

14. The system of claim 12, wherein said light source includes a collimator for limiting a diameter and a dispersion angle of said light beam.

15. The system of claim 12, wherein said optical device includes at least two targets, said targets establishing said alignment axis of said alignment mechanism.

16. The system of claim 15, wherein said optical device includes a target support for maintaining in position said at least two targets.

17. The system of claim 16, wherein a first target of said at least two targets is an aperture on a first surface of said target support, said first surface being perpendicular to said alignment axis.

18. The system of claim 17, wherein a shape of said aperture is selected from the group consisting of a circle, a slit, and a cross.

19. The system of claim 17, wherein a shape of said aperture is filled with a filter, said filter having imprinted thereon an indicator marking.

20. The system of claim 17, wherein a second target of said at least two targets is placed on a second surface of said target support, said second surface being interior of said target support and parallel to and opposite to said first surface.

21. The system of claim 20, wherein said second target is an indicator marking.

22. The system of claim 16, wherein said target support is a cylindrical tube.

23. The system of claim 16, wherein said target support is a prism, said prism having at least three surfaces.

24. The system of claim 23, wherein:

(a) a first target of said at least two targets is placed on a first plane of said prism, said first plane being parallel to a first surface of said prism;

(b) a second target of said at least two targets is placed on a second plane of said prism, said second plane being parallel to a second surface of said prism; and, (c) a third surface of said prism is a mirror.

25. The system of claim 15, wherein said reference guideline and said alignment axis are colinearly aligned by said light beam illuminating all of said at least two targets.

26. The system of claim 1, wherein said optical device includes a light source, said light source producing a light beam.

27. The system of claim 26, wherein said light source is selected from the group consisting of a light emitting diode, a laser, and a fiber optic strand connected to a lamp.

28. The system of claim 26, wherein said light source includes a collimator for limiting a diameter and a dispersion angle of said light beam.

29. The system of claim 26, wherein said optical device further includes a target, said target being fixed in position in said optical device and adapted to establish said alignment axis.

30. The system of claim 29, wherein said reference insert includes a mirror on said reference insert, said mirror being adapted to establish said reference guideline.

31. The system of claim 30, wherein said mirror is on an upper surface of said reference insert.

32. The system of claim 30, wherein said reference insert is hollow, forming a cavity, and wherein said mirror is placed within said cavity.

33. The system of claim 30, wherein said light source and said target are fixed in position in said optical device such that said alignment axis is colinearly aligned with said reference guideline when said light beam incident on said mirror produces a reflected beam, and said reflected beam is colinear with said alignment axis of said target.

34. The system of claim 33, wherein said optical device includes a prism, wherethrough said light beam and said reflected beam pass, said prism having at least three faces.

35. The system of claim 34, wherein said faces are both reflective and transparent to light.

36. The system of claim 35, wherein:

a. said light beam first penetrates a first face of said at least three faces, such that said light beam is bent so as to pass through a second face of said at least three faces and said light beam produces a first image on a third face of said at least three faces;

b. said second face is placeable opposite said reference insert, such that said beam is incident on said reference insert, and said reflected beam passes through said second face so as to be reflected by said first face to produce a second image on said third face; and, c. said first image and said second image are coincident such that only a single representation of said light beam is produced on a plane parallel to said third face when said alignment axis and said reference guideline are colineraly aligned.

37. The system of claim 34, wherein said prism has adjustable angles.

38. The system of claim 1, wherein said optical device includes a threaded fiber optic array with a plurality of fibers with two ends.

39. The system of claim 38, wherein said reference insert includes a mirror on an upper surface of said reference insert, said mirror being adapted to establish said reference guideline.

40. The system of claim 39, wherein said plurality of fibers includes at least one transmitting fiber, with a light source connected to a first end of said two ends, and at least one receiving fiber, with a light receptor at a first end of said two ends.

41. The system of claim 40, wherein said at least one transmitting fiber and said at least one receiving fiber are adapted to establish said alignment axis such that a light beam transmitted from a second end of said at least one transmitting fiber incident upon said mirror and reflected by said mirror is received by said first end of said at least one receiving fiber of said optical device only when said alignment axis and said reference guideline are colineraly aligned.

42. The system of claim 41, wherein a display element is connected to a second end of said at least one receiving fiber of said optical device.

43. The system of claim 42, wherein said display element is selected from the group consisting of a lens on said second end of said at least one receiving fiber, a miniature screen, an optical display, a photosensitive cell and a light detector.

44. The system of claim 43, wherein said light detector is connected to a signaling device.

45. The system of claim 44, wherein said signaling device produces an audible signal.

46. The system of claim 1, wherein the system is used for drilling the hole in bone for a dental implant.

47. The system of claim 1, wherein the system is used for drilling the hole in bone for an orthopedic fixation appliance.

48. A method for positioning a drill for drilling a subsequent hole in a bone at a predetermined distance from, and in a predetermined orientation in respect to, a reference hole, the drill having a drill bit with a central axis, the method comprising the steps of:

(a) inserting a reference insert into the reference hole, said reference insert being adapted to establish a reference guideline, said reference guideline being of the predetermined orientation;

(b) providing an alignment mechanism, attached to the drill, said alignment mechanism adapted to be fixed at the predetermined distance from and parallel to the central axis of the drill bit, said alignment mechanism including an optical device for colinearly aligning an alignment axis of said alignment mechanism with said reference guideline;

(c) fixing said alignment mechanism at the predetermined distance; and, (d) aligning said alignment axis of said optical device of said alignment mechanism with said reference guideline, thereby positioning the drill at the predetermined distance from and in the predetermined orientation in respect to the reference hole.

49. The method of claim 48, wherein the method is used for drilling the hole in bone for a dental implant.

50. The method of claim 48, wherein the method is used for drilling the hole in bone for an orthopedic fixation appliance.

* * * * *